(12) United States Patent
Sone et al.

(10) Patent No.: US 11,661,383 B2
(45) Date of Patent: *May 30, 2023

(54) METHANE SYNTHESIS DEVICE

(71) Applicant: Japan Aerospace Exploration Agency, Chofu (JP)

(72) Inventors: Yoshitsugu Sone, Chofu (JP); Omar Mendoza, Chofu (JP); Asuka Shima, Chofu (JP); Takayuki Abe, Toyama (JP); Mitsuhiro Inoue, Toyama (JP); Hiroshige Matsumoto, Fukuoka (JP); Yuki Terayama, Fukuoka (JP); Motohiko Sato, Sagamihara (JP)

(73) Assignee: JAPAN AEROSPACE EXPLORATION AGENCY, Chofu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/708,838

(22) Filed: Mar. 30, 2022

(65) Prior Publication Data

US 2022/0267232 A1     Aug. 25, 2022

Related U.S. Application Data

(63) Continuation of application No. 16/758,828, filed as application No. PCT/JP2018/041877 on Nov. 12, 2018, now Pat. No. 11,492,301.

(30) Foreign Application Priority Data

Nov. 10, 2017    (JP) .................................. 2017-217736

(51) Int. Cl.
   *C07C 1/12*         (2006.01)
   *C25B 9/015*        (2021.01)
   (Continued)

(52) U.S. Cl.
   CPC ................. *C07C 1/12* (2013.01); *B01J 35/04* (2013.01); *C25B 1/04* (2013.01); *C25B 3/03* (2021.01);
   (Continued)

(58) Field of Classification Search
   CPC ............................... C25B 1/04; C25B 15/081
   See application file for complete search history.

(56) References Cited

U.S. PATENT DOCUMENTS

| 8,710,106 B2 | 4/2014 | Junaedi et al. |
| 2015/0191834 A1 | 7/2015 | Patru et al. |

(Continued)

FOREIGN PATENT DOCUMENTS

| JP | 2005-281198 A | 10/2005 |
| JP | 2015-513531 A | 5/2015 |
| JP | 5759687 B2 | 8/2015 |

OTHER PUBLICATIONS

International Search Report dated Jan. 22, 2019, issued in connection with International Application No. PCT/JP2018/041877, filed on Nov. 12, 2018, 3 pages.

(Continued)

*Primary Examiner* — Brian W Cohen
(74) *Attorney, Agent, or Firm* — McDonnell Boehnen Hulbert & Berghoff LLP

(57) ABSTRACT

An object is to provide a methane synthesis device having as a whole a reduced size and a simplified configuration. A methane synthesis device 100 is composed of respective components from an end plate 2 at the leftmost side to an end plate 23 at the rightmost side and is compactly assembled by fastening plural bolts and nuts to bring these individual components into tightly contact with each other. The components may be divided into a Sabatier reaction unit of signs 3 to 9, a water electrolysis unit of signs 13 to 19, and other (Continued)

components. Hydrogen gas generated in the water electrolysis unit is mixed with carbon dioxide gas and supplied to the Sabatier reaction unit, and methane is synthesized in the Sabatier reaction unit. The size of the device is reduced as a whole and configuration is simplified by integrally stacking the water electrolysis unit, the Sabatier reaction unit, a carbon dioxide supplying unit, and a hydrogen gas supplying unit.

3 Claims, 15 Drawing Sheets

(51) Int. Cl.
   *C25B 9/77* (2021.01)
   *C25B 3/03* (2021.01)
   *C25B 11/053* (2021.01)
   *B01J 35/04* (2006.01)
   *C25B 1/04* (2021.01)
   *C25B 15/08* (2006.01)
(52) U.S. Cl.
   CPC ............... *C25B 9/015* (2021.01); *C25B 9/77* (2021.01); *C25B 11/053* (2021.01); *C25B 15/081* (2021.01)

(56) References Cited

U.S. PATENT DOCUMENTS

2016/0017800 A1  1/2016  Simpson
2016/0107952 A1  4/2016  Schulz

OTHER PUBLICATIONS

Written Opinion dated Jan. 22, 2019, issued in connection with International Application No. PCT/JP2018/041877, filed on Nov. 12, 2018, 3 pages.

METHANE SYNTHESIS DEVICE

CROSS-REFERENCE TO RELATED APPLICATIONS

This application is a continuation of U.S. application Ser. No. 16/758,828, filed Apr. 23, 2020, which is a U.S. National Phase Application under 35 U.S.C. § 371 of International Application No. PCT/JP2018/041877, filed Nov. 12, 2018, which claims priority to Japanese Patent Application No. 2017-217736, filed Nov. 10, 2017, the contents of each of which is incorporated herein by reference in its entirety.

FIELD OF THE INVENTION

The present invention relates to a methane synthesis device for synthesizing methane by utilizing hydrogen generated through water electrolysis.

BACKGROUND OF THE INVENTION

As the application of renewable energy is expected to be expanded, an attempt to use renewable energy for electrolyzing water to generate hydrogen and utilize the generated hydrogen as a resource through combustion or fuel cell reaction has been carried out. Furthermore, a study for synthesizing methane by reacting hydrogen generated through water electrolytic reaction and carbon dioxide in the air and utilizing the synthesized methane as an energy carrier has been conducted. Methane is expected to be used as a replacement for natural gas, and even carbon dioxide is emitted through the utilization of methane thus obtained as a replacement for natural gas, carbon dioxide originating from the air merely returns into the air, and therefore excess carbon dioxide is not emitted. In addition, methane may retain three-fourths of energy compared to the same volume of hydrogen in terms of density. Therefore, utilization of methane as an excellent energy carrier is expected.

Sabatier reaction is known as a technique for synthesizing methane by reacting hydrogen and carbon dioxide. This reaction is a technique to catalytically react hydrogen and carbon dioxide to generate methane and water, and since the carbon dioxide reduction rate by hydrogen in this reaction reaches approximately 100% at about 350° C., highly efficient reduction of carbon dioxide gas is possible. Moreover, since this reaction is exothermic autonomous reaction, and the reaction is capable of being maintained without externally supplying thermal energy or the like, efficient conversion from renewable energy to an energy carrier is expected to be made possible by applying Sabatier reaction.

It has been known heretofore that methane may be generated by utilizing hydrogen generated through water electrolytic reaction for Sabatier reaction, and the combination of these reactions is actually proposed to generate methane. In a conventionally known device, separate reaction tanks are provided for water electrolytic reaction and Sabatier reaction, and hydrogen generated in the tank for water electrolysis is once stored and then supplied to the tank for Sabatier reaction or even hydrogen is not stored, hydrogen generated in the tank for water electrolysis is supplied to the tank for Sabatier reaction through dedicated piping to generate methane. Consequently, the device as a whole becomes large and bulky, and the entire configuration thereof also becomes complicated (see Patent document 1, for example).

CITATION LIST

Patent Literature

Patent Document 1: Japanese Patent Laid-Open No. 2005-281198

SUMMARY OF INVENTION

Problem to be Solved by the Invention

In view of the above, the present invention aims at overcoming the above-described problem and providing a methane synthesis device having as a whole a reduced size and a simplified configuration.

Means for Solving Problem

A methane synthesis device according to the present invention includes a water electrolysis unit including a hydrogen side electrode membrane, an electrolyte membrane, an oxygen side electrode membrane, and a water supplying section supplying liquid water from any of a side of the hydrogen side electrode membrane and a side of the oxygen side electrode membrane to a surface of the electrolyte membrane;

a Sabatier reaction unit provided adjacent to the hydrogen side electrode membrane of the water electrolysis unit;

a carbon dioxide supplying unit supplying carbon dioxide-containing gas to the Sabatier reaction unit; and a hydrogen gas supplying unit supplying hydrogen gas generated through electrolyzation of water in the water electrolysis unit to the Sabatier reaction unit, wherein methane gas is synthesized by Sabatier reaction between the carbon dioxide-containing gas and the hydrogen gas supplied to the Sabatier reaction unit.

The water electrolysis unit, the Sabatier reaction unit, the carbon dioxide supplying unit, and the hydrogen gas supplying unit may be integrally stacked, and the Sabatier reaction unit may be stacked on a side of the hydrogen side electrode membrane of the water electrolysis unit.

Heat of reaction generated in the Sabatier reaction unit may be supplied to the water electrolysis unit.

A plurality of slits and a plurality of ladder-shaped parts between slits may be formed on the hydrogen side electrode membrane, a gas separator may be disposed at a side of the hydrogen side electrode membrane opposite to the electrolyte membrane, a plurality of grooves may be formed on the gas separator at the side contacting the hydrogen side electrode membrane so that the plurality of grooves are aligned with the plurality of slits of the hydrogen side electrode membrane, and the water supplying section may supply liquid water to a surface of the electrolyte membrane via the plurality of grooves of the gas separator and the plurality of slits of the hydrogen side electrode membrane.

A vent hole penetrating to another face may be formed in the ladder-shaped parts between the plurality of slits of the hydrogen side electrode membrane, and the vent hole may allow hydrogen gas generated through electrolyzation of water in the water electrolysis unit to pass and to be supplied to the hydrogen gas supplying unit.

Further, a gas mixing unit may be provided, and the gas mixing unit may allow the carbon dioxide-containing gas supplied from the carbon dioxide supplying unit and the hydrogen gas supplied from the hydrogen gas supplying unit to be mixed in a gas flow passage formed inside the gas mixing unit and may supply the mixed carbon dioxide-containing gas and hydrogen gas to the Sabatier reaction unit.

A first gas separator may be disposed between the Sabatier reaction unit and the hydrogen side electrode membrane, the water supplying section may be placed at the side of the oxygen side electrode membrane and may supply liquid water to a surface of the electrolyte membrane from the side of the oxygen side electrode membrane, and the first gas separator may allow hydrogen gas separated from liquid water to pass between the hydrogen side electrode membrane and the electrolyte membrane to be directly supplied to the Sabatier reaction unit.

A plurality of slits and a plurality of ladder-shaped parts between slits may be formed on the oxygen side electrode membrane, a second gas separator allowing oxygen-containing gas separated from liquid water to pass may be disposed at a side of the oxygen side electrode membrane opposite to the electrolyte membrane, a plurality of grooves may be formed on the second gas separator at the side contacting the oxygen side electrode membrane so that the plurality of grooves is aligned with the plurality of slits of the oxygen side electrode membrane, and the water supplying section may supply liquid water to a surface of the electrolyte membrane via the plurality of grooves of the second gas separator and the plurality of slits of the oxygen side electrode membrane.

The Sabatier reaction unit may include a porous metal mesh and a Sabatier catalyst supported by the porous metal mesh.

A methane gas flowing unit in which the methane gas flows may be provided adjacent to the Sabatier reaction unit.

Effect of the Invention

As mentioned above, since the water electrolysis unit and the Sabatier reaction unit are adjacent to each other in the methane synthesis device of the present invention, reduction in size of the device as a whole is made possible. In addition, since the water electrolysis unit and the Sabatier reaction unit are adjacent to each other, methane gas may be rapidly generated from hydrogen generated through water electrolytic reaction. Furthermore, enhancement of water electrolytic reaction efficiency and prevention of thermal runaway of the methane synthesis device as a whole are made possible by effectively utilizing the latent heat of water used for water electrolysis and heat generated by Sabatier reaction.

DESCRIPTION OF EMBODIMENTS

Hereinafter, embodiments of the present invention will be described with reference to figures. Incidentally, the present invention is not limited to the embodiments described below.

Embodiment 1

Figure 1:
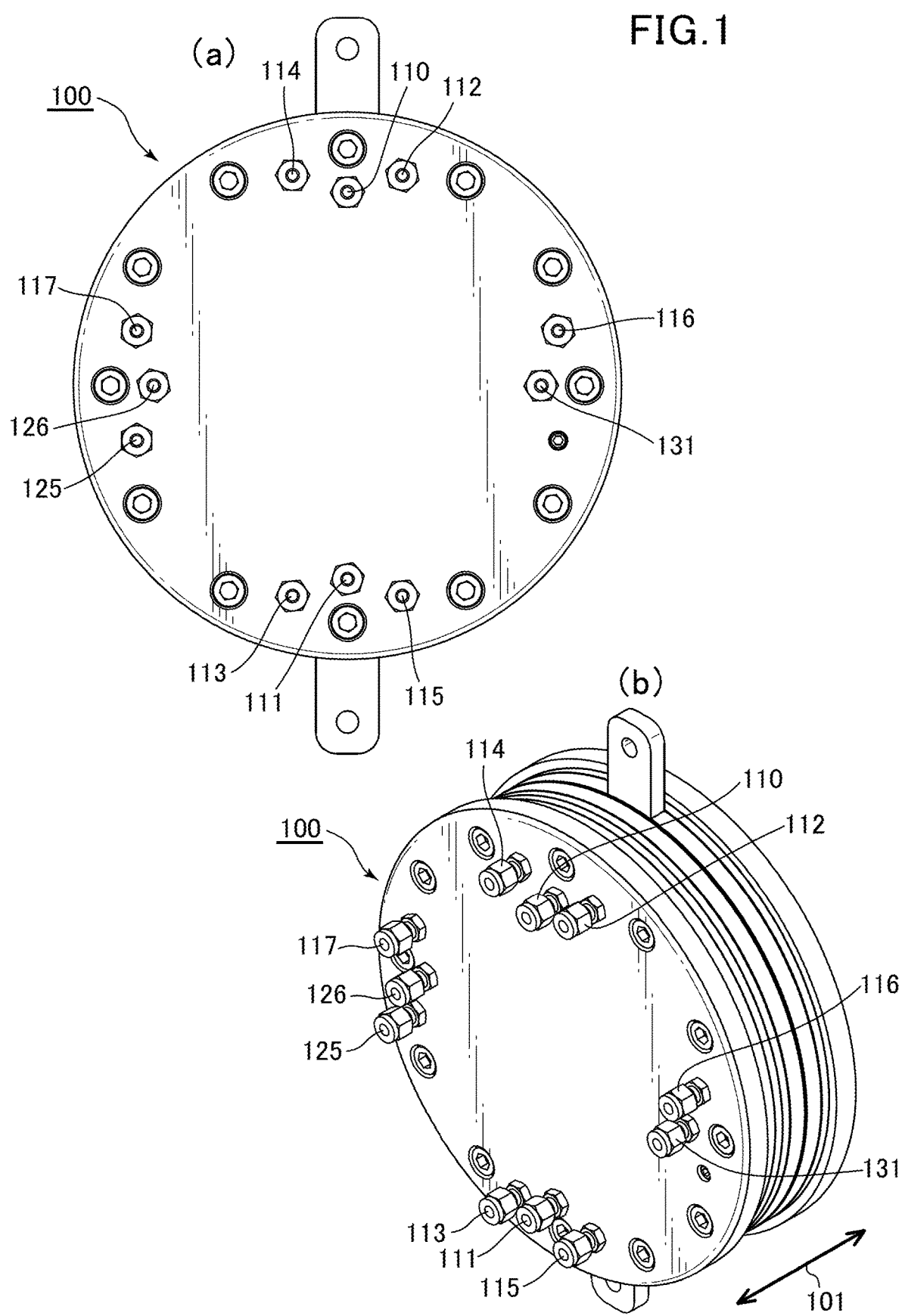
FIG. 1 shows a front view ((a) in the figure) and a perspective view ((b) in the figure) of a methane synthesis device 100 according to Embodiment 1.
Figure 2:
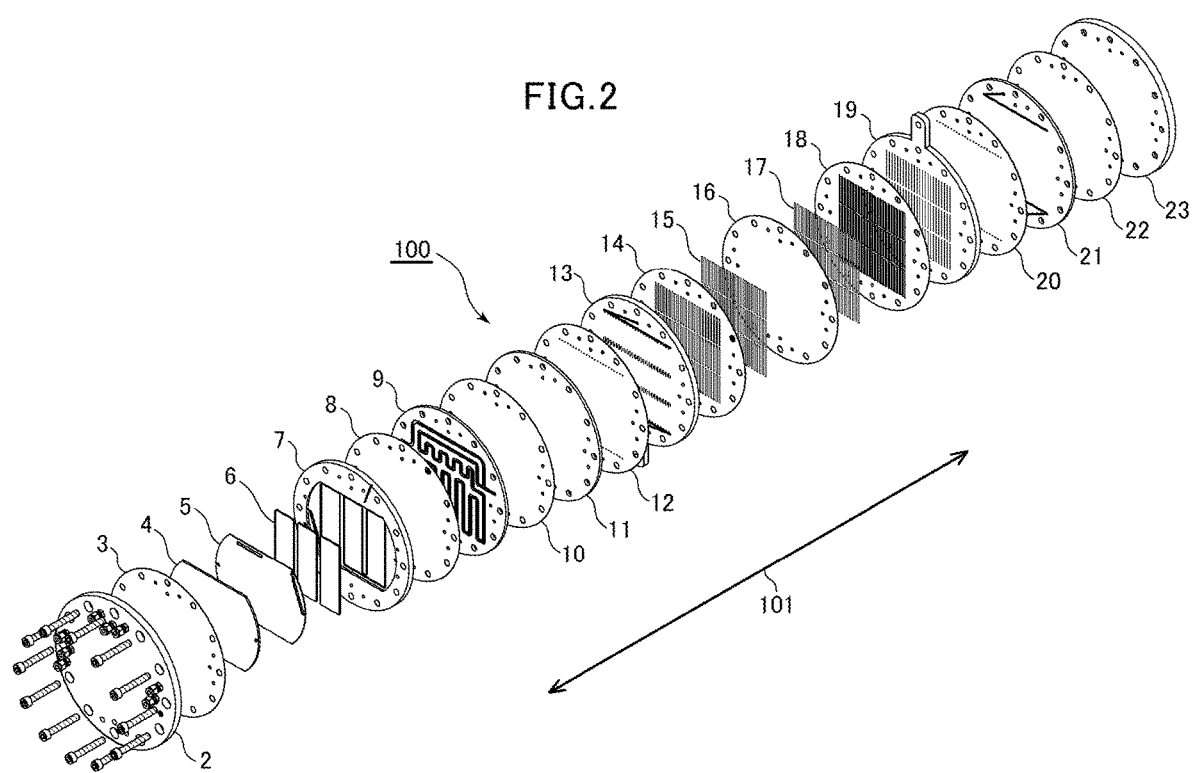
FIG. 2 is an exploded view showing individual components of the methane synthesis device shown in FIG. 1 separated from each other.

FIG. 1 shows a front view ((a) in the figure) and a perspective view ((b) in the figure) of a methane synthesis device 100 according to Embodiment 1, and FIG. 2 is an exploded view showing individual components of the methane synthesis device 100 shown in FIG. 1 separated from each other in the direction of an arrow 101 in the figure. The methane synthesis device 100 is composed of respective components shown in FIG. 2 from an end plate 2 at the leftmost side to an end plate 23 at the rightmost side and is compactly assembled by fastening plural bolts and nuts to bring these individual components into tightly contact with each other as shown in FIG. 1. The components shown in FIG. 2 may be divided into a Sabatier reaction unit of signs 3 to 9, a water electrolysis unit of signs 13 to 21, and other components.

Figure 3:
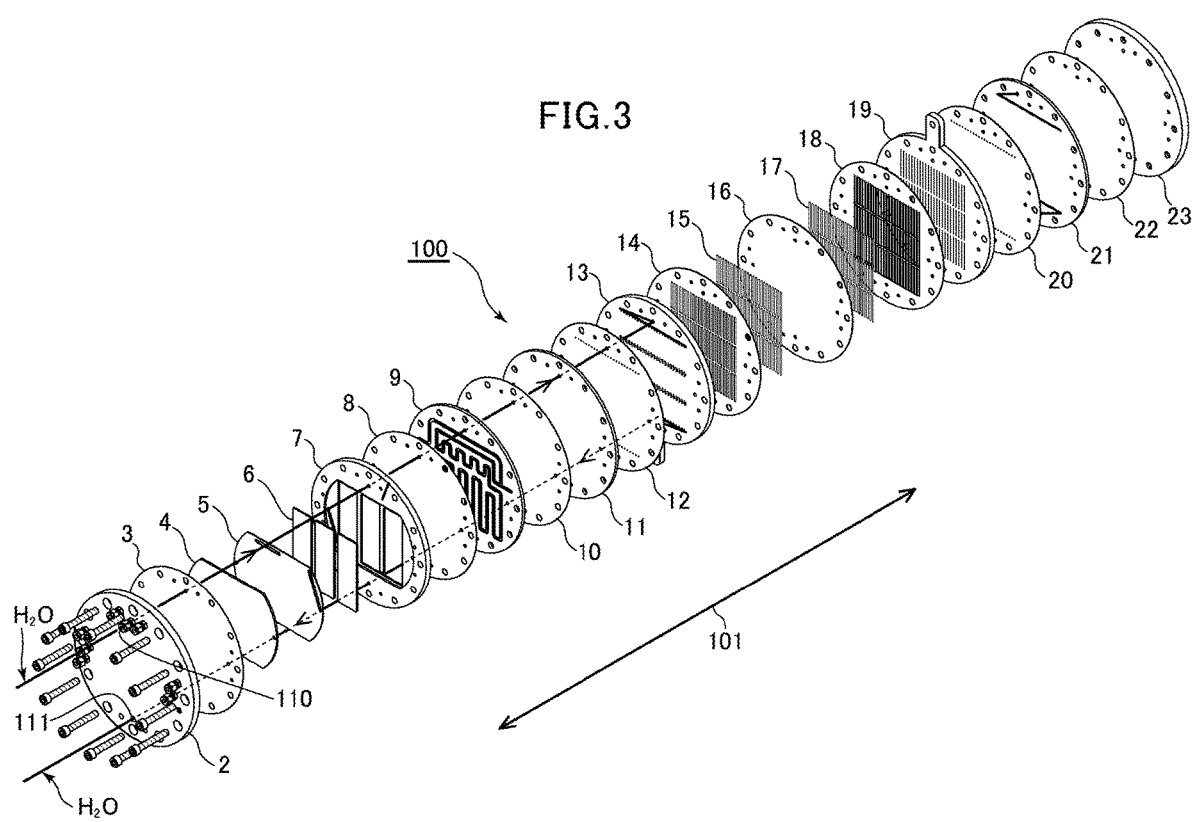
FIG. 3 simply shows an overall pathway of liquid water (H₂O) flowing in the methane synthesis device shown in FIG. 2.

First, the water electrolysis unit will be described. FIG. 3 shows an overall pathway of liquid water (H₂O) flowing in the methane synthesis device 100 shown in FIG. 2. Liquid water supplied from the outside enters a water inlet 110, is sent to a gas separator 13 (first gas separator) of the water electrolysis unit, and is used for water electrolytic reaction. Water not used for the reaction is sent from the gas separator 13 to a water outlet 111 in the end and discharged to the outside.

Figure 4:
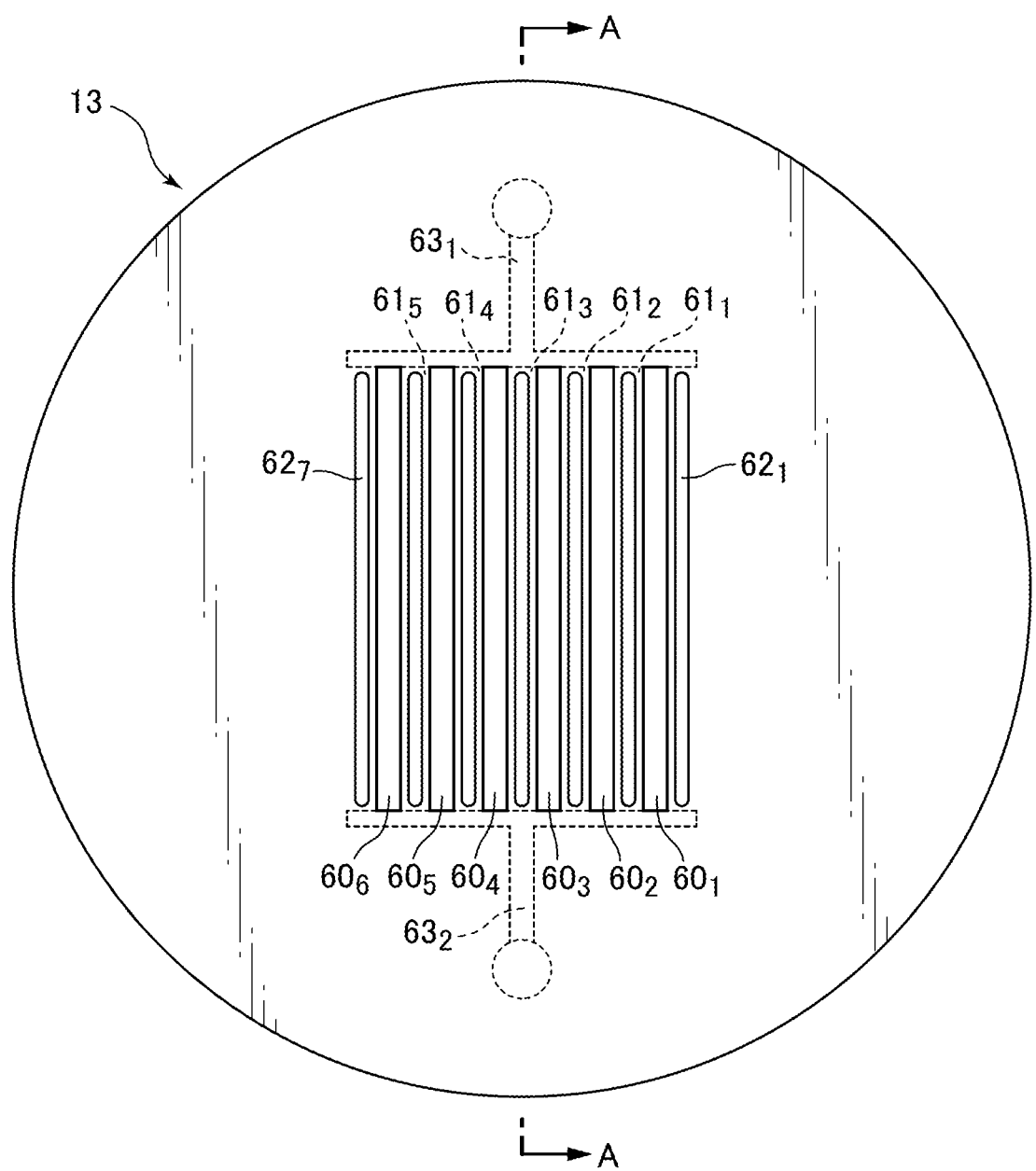
FIG. 4 shows a part of a face of the gas separator shown in FIG. 2 on the right side in FIG. 2.
Figure 5:
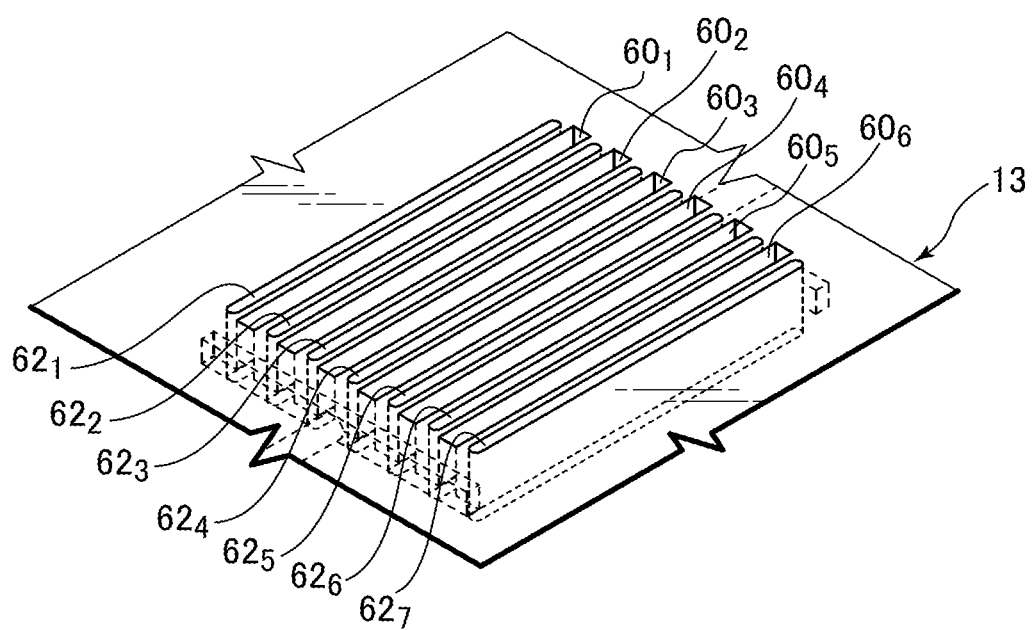
FIG. 5 is a perspective view showing only a part of grooves and plate-like parts of the gas separator shown in FIG. 4.

FIG. 4 shows a part of a face of the gas separator 13 shown in FIG. 2 on the right side in FIG. 2 (a face invisible in FIG. 2). Note that the number and arrangement of the grooves formed on this face are different from those actually employed. As shown in FIG. 4, a plurality of long thin parallel grooves $60_1$ to $60_6$ bored in the thickness direction (the direction vertical to the paper surface of FIG. 4) of the gas separator 13 is formed in the center part of the gas separator 13. While none of the grooves $60_1$ to $60_6$ penetrates through the gas separator 13, each of the grooves $60_1$ to $60_6$ connects with water flow passages $63_1$ and $63_2$ through both end parts thereof. In addition, long thin plate-like parts $61_1$ to $61_5$ are formed between the grooves. FIG. 5 is a perspective view showing only a part of the grooves $60_1$ to $60_6$ and the plate-like parts $61_1$ to $61_5$ shown in FIG. 4. As shown in FIG. 5, long thin gas flow passages $62_1$ to $62_7$ are provided at the plate-like parts $61_1$ to $61_5$ and both side edges parallel to the plate-like parts $61_1$ to $61_5$. Each of the gas flow passages $62_1$ to $62_7$ penetrates to the back side of the gas separator 13.

Figure 6:
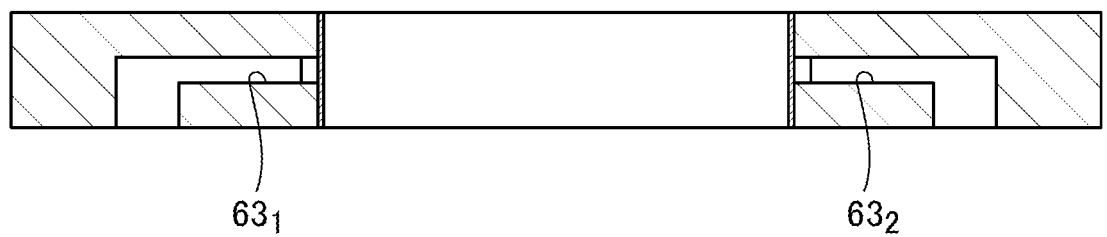
FIG. 6 is a cross-sectional view cut along A-A in FIG. 4 vertically to the paper surface and parallel to the grooves.

FIG. 6 is a cross-sectional view cut along A-A in FIG. 4 in the direction vertical to the paper surface and parallel to the grooves $60_1$ to $60_6$. As shown in the same figure, water flow passages $63_1$ and $63_2$ are each formed in a tunnel shape inside the gas separator 13. One end of the water flow passage $63_1$ connects to the water inlet 110 shown in FIG. 1 via a hole in an upper part of the gas separator 13, and the other end connects to each of the grooves $60_1$ to $60_6$. In addition, one end of the water flow passage $63_2$ connects to the water outlet 111 via a hole in a lower part of the gas separator 13, and the other end connects to each of the grooves $60_1$ to $60_6$.

Figure 7:
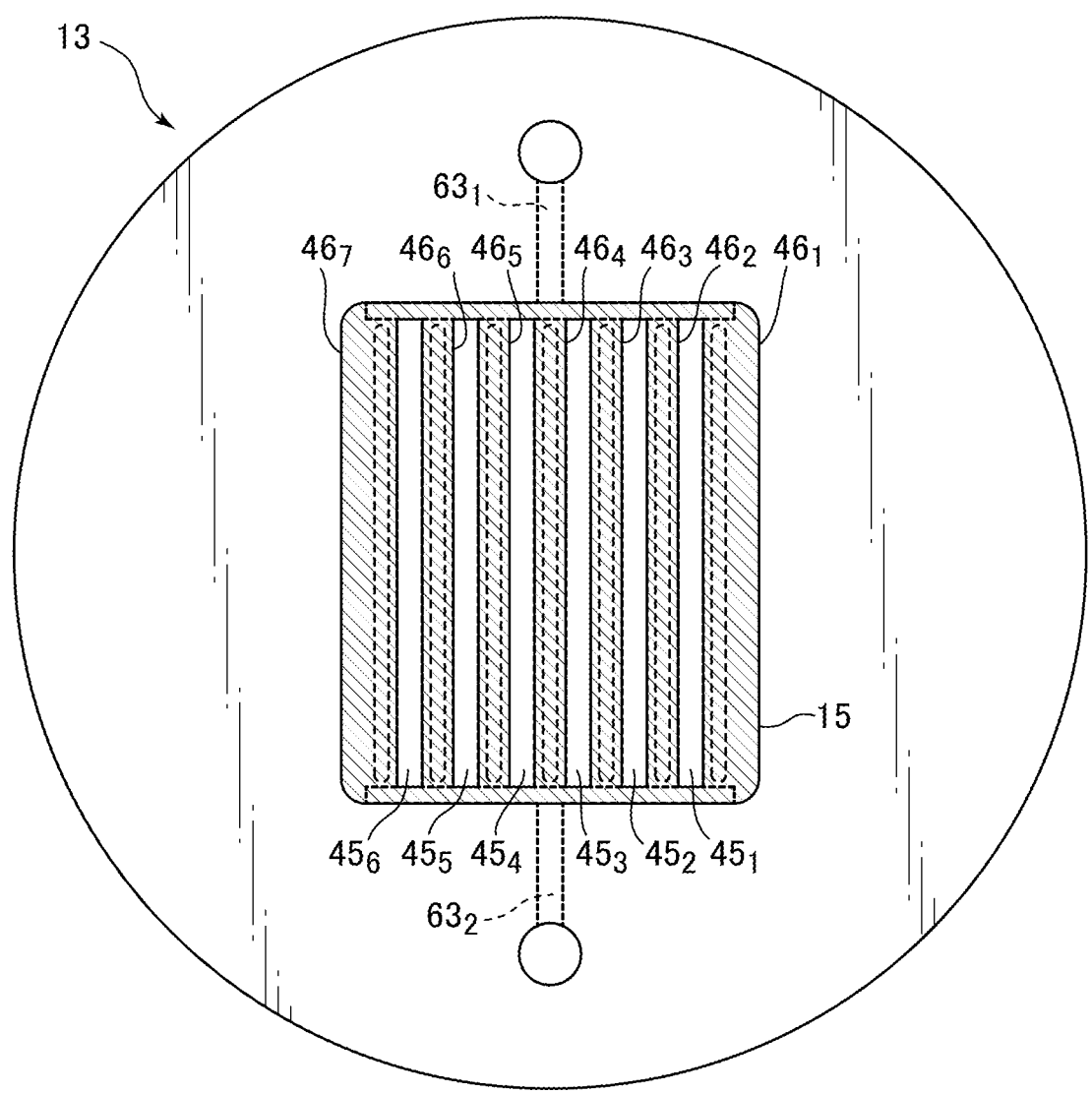
FIG. 7 is a plan view showing the positional relationship between a gas separator and a hydrogen side electrode membrane fitted in a gasket when the methane synthesis device has been assembled.

FIG. 7 is a plan view showing the positional relationship between the gas separator 13 and a hydrogen side electrode membrane 15 fitted in a gasket 14 when the methane synthesis device 100 has been assembled. As shown in FIG. 7, each of slits $45_1$ to $45_6$ provided on the hydrogen side electrode membrane 15 is aligned with the corresponding grooves $60_1$ to $60_6$ provided on the gas separator 13. Ladder-shaped members $46_1$ to $46_7$ between the slits of the hydrogen side electrode membrane 15 are aligned with the corresponding plate-like parts $61_1$ to $61_5$ of the gas separator 13 and the both side edges parallel to the plate-like parts $61_1$ to $61_5$ and close the gas flow passages $62_1$ to $62_7$ provided at the plate-like parts $61_1$ to $61_5$ and the both side edges. Consequently, water is prevented from entering into the gas flow passages $62_1$ to $62_7$ as described later.

Liquid water is introduced into the multiple grooves $60_1$ to $60_6$ provided on the gas separator 13 from the hole provided in the upper part of the gas separator 13 shown in FIG. 3 through the water flow passage $63_1$ inside the gas separator 13 shown in FIG. 4. Then, water is supplied from these multiple grooves $60_1$ to $60_6$ to an electrolyte membrane 16 through the surface thereof. Thereafter, excess water is discharged from the water outlet 111 through the water flow passage $63_2$ provided in the opposite side of the gas separator 13 and the hole provided in the lower part of the gas separator 13. While the overall pathway through which water flows shown in FIG. 3 extends parallel to the arrow 101, the water flow passages $63_1$ and $63_2$ formed inside the gas separator 13 extend in the direction vertical to the arrow 101, that is, in the direction vertical to the stacked direction of the methane synthesis device 100.

Figure 8:
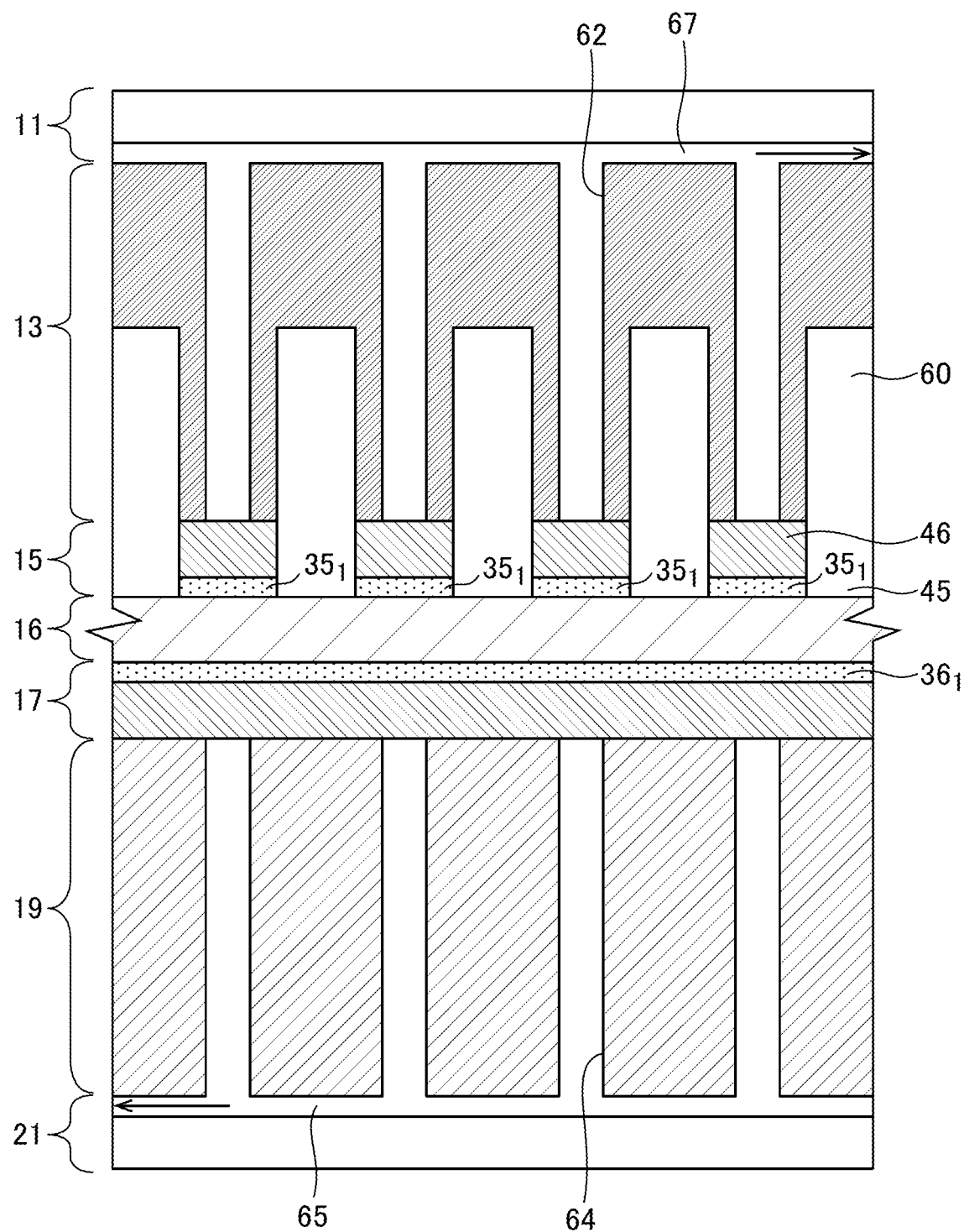
FIG. 8 is an enlarged view schematically showing a cross-section of a water electrolysis unit, which is obtained by bringing individual components including the gas separator, gasket, hydrogen side electrode membrane, electrolyte membrane, oxygen side electrode membrane, gasket, and gas separator at oxygen side shown in FIG. 2 into tightly contact with each other, cut vertically to the plate-like parts.

FIG. 8 is an enlarged view schematically showing a cross-section of the water electrolysis unit, which is obtained by bringing individual components including the gas separator 13, gasket 14, hydrogen side electrode membrane 15, electrolyte membrane 16, oxygen side electrode membrane 17, gasket 18, and gas separator at oxygen side 19 (second gas separator) shown in FIG. 2 into tightly contact with each other, cut vertically to the plate-like parts $61_1$ to $61_5$ in contrast to FIG. 6.

Proton ($H^+$) conductive porous electrolytes may be used as a solid electrolyte composing the electrolyte membrane 16. Inorganic ceramics shown in Japanese Patent No. 5759687 (for example, hydrous titanium oxide nanoparticles) may be preferably used as a specific material, for example. Proton conductive Nafion (R), which is a dense electrolyte, or the like may also be used as another example of the solid electrolyte composing the electrolyte membrane 16.

Teflon (R)-modified porous carbon shown in Japanese Patent No. 5759687 may be preferably used as a material for the hydrogen side electrode membrane 15 and the oxygen side electrode membrane 17 between which the electrolyte membrane 16 is sandwiched, for example. The use of this material enables oxygen gas and hydrogen gas to permeate the inside thereof. In addition, the hydrogen side electrode membrane 15 and the oxygen side electrode membrane 17 are subjected to water repellent treatment as a whole and have strong water repellency. Consequently, water may be prevented from invading the inside of the hydrogen side electrode membrane 15 and the oxygen side electrode membrane 17.

Catalyst layers $35_1$ and $36_1$ are respectively formed on a surface of the hydrogen side electrode membrane 15 and a surface of the oxygen side electrode membrane 17, with each of the surfaces being on the side joining to the electrolyte membrane 16. Platinum-carrying carbon shown in Japanese Patent No. 5759687 may be preferably used as a catalyst material. A catalyst of about several atomic layers is enough. Therefore, a method in which a catalyst material is atomized and sprayed by a spray may be applied, for example. In addition, while the catalyst layers are formed on the hydrogen side electrode membrane 15 and the oxygen side electrode membrane 17 herein, a catalyst layer may be formed on a surface of the electrolyte membrane 16.

Figure 9:
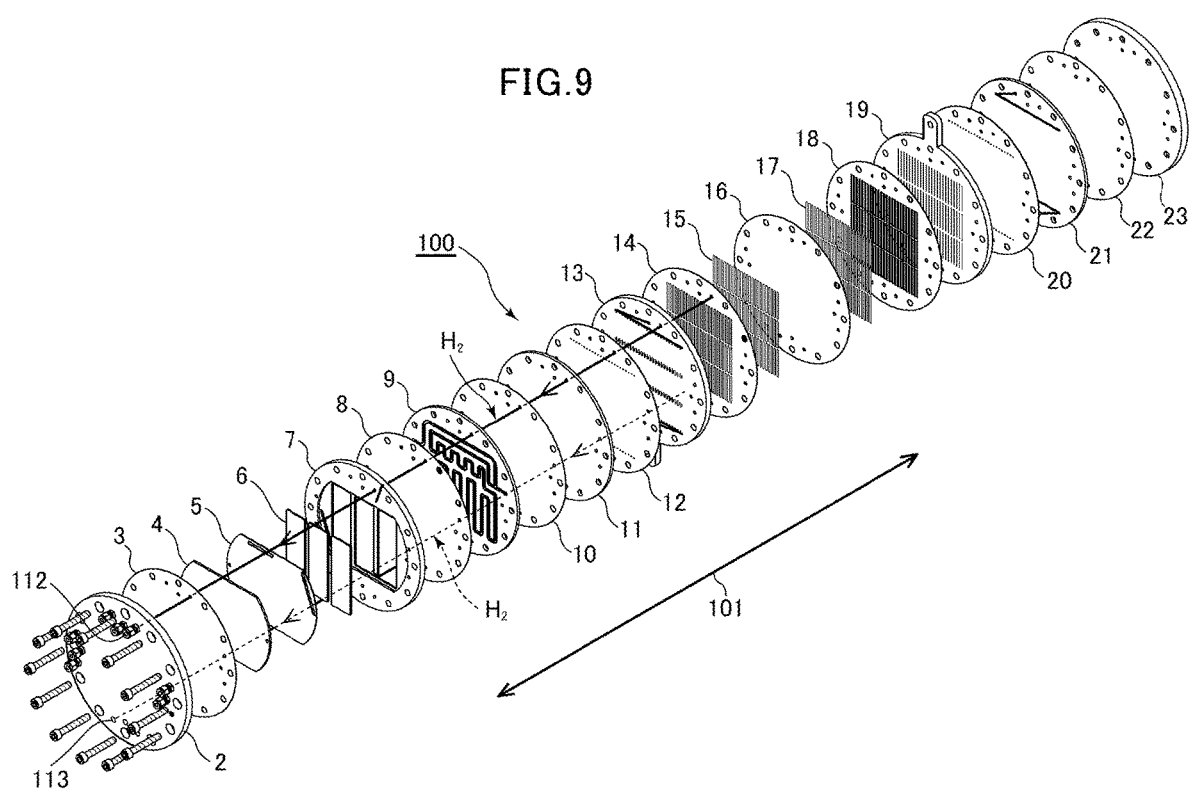
FIG. 9 shows a pathway through which hydrogen gas generated in the water electrolysis unit is once discharged to the outside of the device.

On electrolyzation of water, when negative voltage and positive voltage are applied to the hydrogen side electrode membrane 15 and the oxygen side electrode membrane 17, respectively, hydrogen gas generated at the interface (catalyst layer) between the hydrogen side electrode membrane 15 and the electrolyte membrane 16 permeates the ladder-shaped members $46_1$ to $46_7$ of the hydrogen side electrode membrane 15, is carried to the corresponding gas flow passages $62_1$ to $62_7$ provided in the gas separator 13, flows through a gas flow passage 67 formed at the front of a metal plate 11, and is sent to gas outlets 112, 113 provided at the end plate 2 to be discharged once in the pathway shown in FIG. 9.

Figure 10:
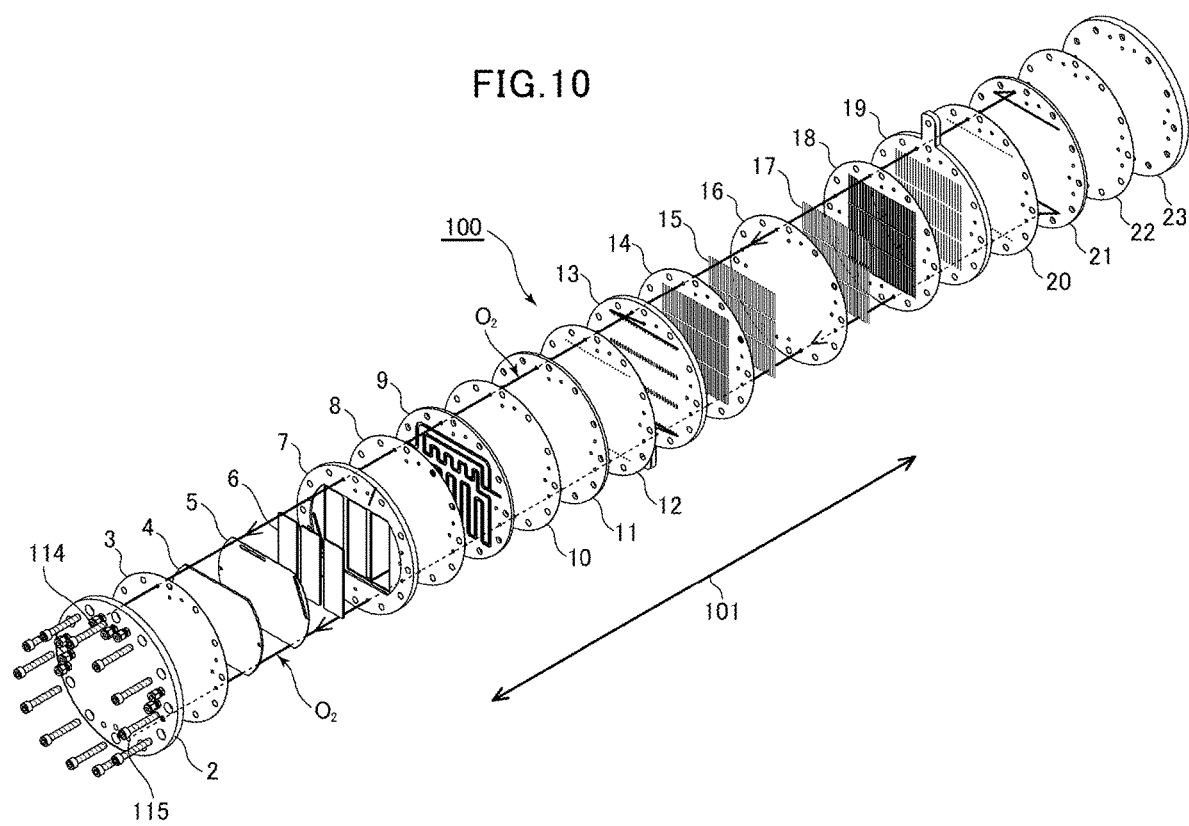
FIG. 10 shows a pathway through which oxygen gas generated in the water electrolysis unit is discharged to the outside of the device.

On the other hand, oxygen gas generated at the interface (catalyst layer) between the oxygen side electrode membrane 17 and the electrolyte membrane 16 permeates the inside of the planar oxygen side electrode membrane 17 while being diffused, is carried to a gas flow passage 64 of the gas separator 19, flows through a gas flow passage 65 formed at the front of a metal plate 21 through the gas flow passage 64, and is sent to gas outlets 114, 115 provided at the end plate 2 to be discharged in the pathway shown in FIG. 10.

As described above, the hydrogen side electrode membrane 15 and the oxygen side electrode membrane 17 have strong water repellency. Consequently, water supplied from the outside to the electrolyte membrane 16 through the water flow passage 63, grooves $60_1$ to $60_6$, and slits $45_1$ to $45_6$ never enters the hydrogen side electrode membrane 15 or the oxygen side electrode membrane 17. Accordingly, the pathways of oxygen gas and hydrogen gas are completely separated from the pathway of water, and these pathways are never mixed. In addition, water is directly supplied to the surface of the electrolyte membrane 16 composed of a solid electrolyte in the water electrolysis unit of the present embodiment. The water supplied is blocked by the hydrogen side electrode membrane 15 and the oxygen side electrode membrane 17, which have water repellency, and does not invade the insides of the hydrogen side electrode membrane 15 and the oxygen side electrode membrane 17 or the insides of the gas separators 13, 19. That is, the water pathway, the oxygen gas pathway, and the hydrogen gas pathway are completely independent of each other and separated from each other.

Figure 11:
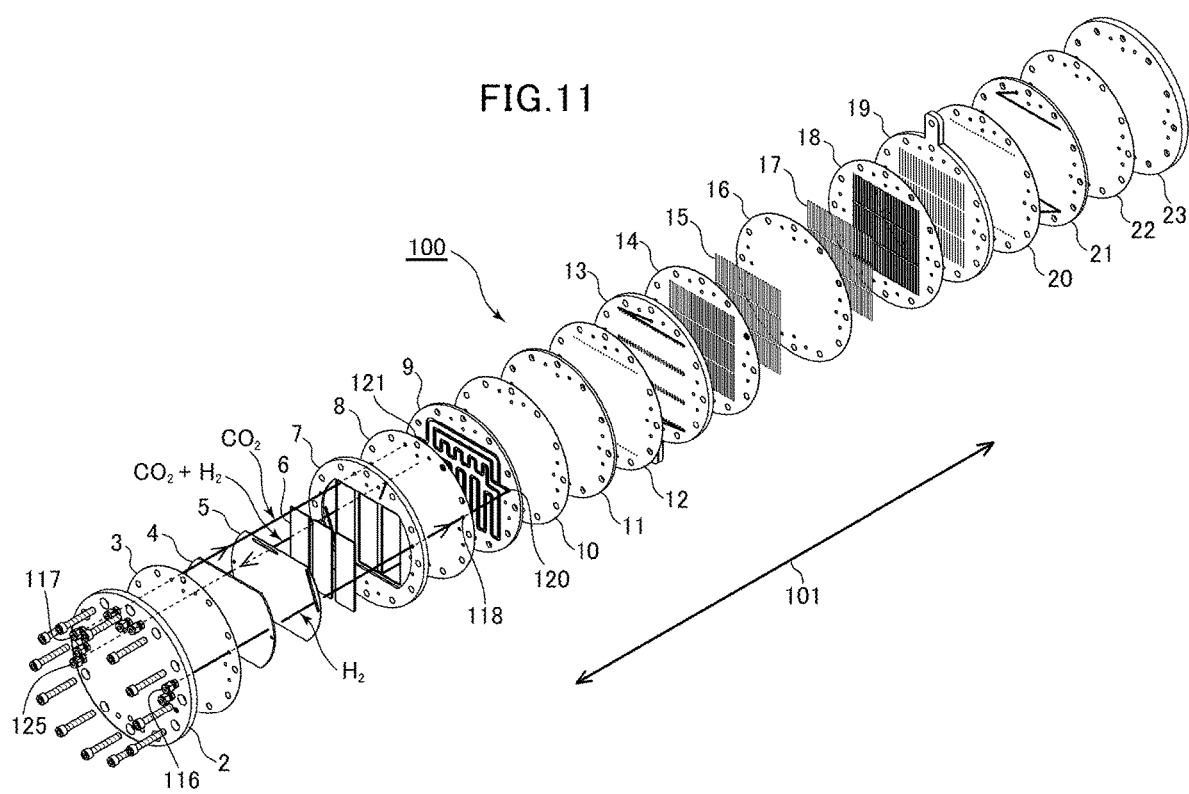
FIG. 11 shows a pathway in which hydrogen gas and carbon dioxide gas are mixed.

Next, the Sabatier reaction unit will be described. The hydrogen gas generated by the water electrolysis unit and once discharged from the gas outlets 112, 113 described above (see FIG. 9) is introduced into the inside of the device again from a gas inlet 116 and sent to one small hole 118 of a cover plate 8 as shown in FIG. 11. On the other hand, carbon dioxide gas introduced separately from hydrogen gas from a gas inlet 117 is sent to another small hole 119 of the cover plate 8. As shown in FIG. 11, a gas mixing plate 9 is disposed next to the cover plate 8 so that the gas mixing plate 9 contacts with the cover plate 8.

Figure 12:
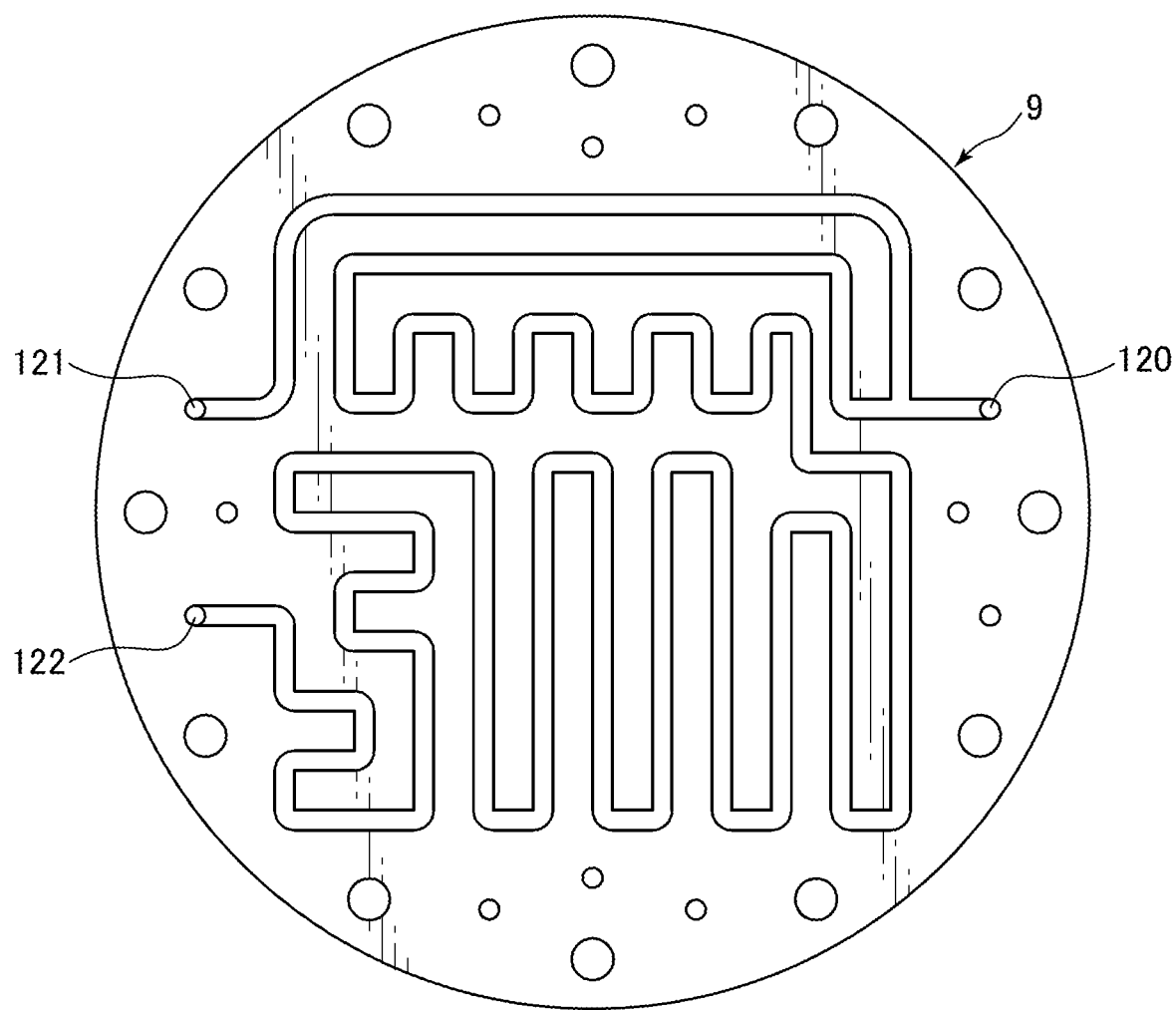
FIG. 12 is a front view of a gas mixing plate.

FIG. 12 is a front view of the gas mixing plate 9. As shown in the same figure, a thin groove is formed over the approximately whole surface of one side of the gas mixing plate 9. This groove serves as a gas passage through which gas flows when the gas mixing plate 9 and the cover plate 8 are brought into tightly contact with each other. The part denoted by sign 120 in the gas mixing plate 9 corresponds to the position of the small hole 118 of the cover plate 9, and hydrogen gas is introduced therefrom. On the other hand, the part denoted by sign 121 in the gas mixing plate 9 corresponds to the position of the small hole 119 of the cover plate 9, and carbon dioxide gas is introduced therefrom. The introduced hydrogen gas and carbon dioxide gas are mixed while flowing through the thin long gas passage. When this mixed gas reaches the part denoted by sign 122 in the gas mixing plate 9, the mixed gas is once discharged to the outside of the device from a gas outlet 125 as shown in FIG. 11 through another small hole (not shown) provided at the cover plate 8.

Figure 13:
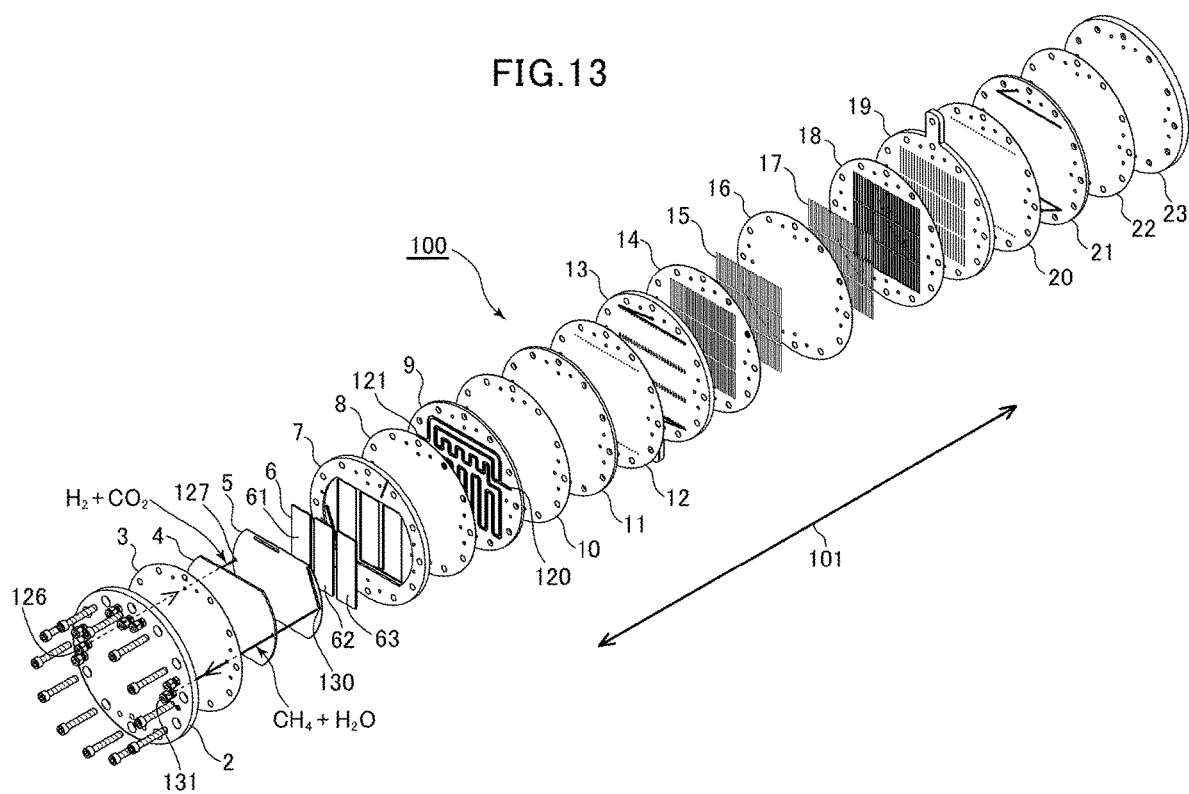
FIG. 13 shows a pathway through which mixed gas containing hydrogen gas and carbon dioxide gas is supplied to a Sabatier reaction catalyst.
Figure 14:
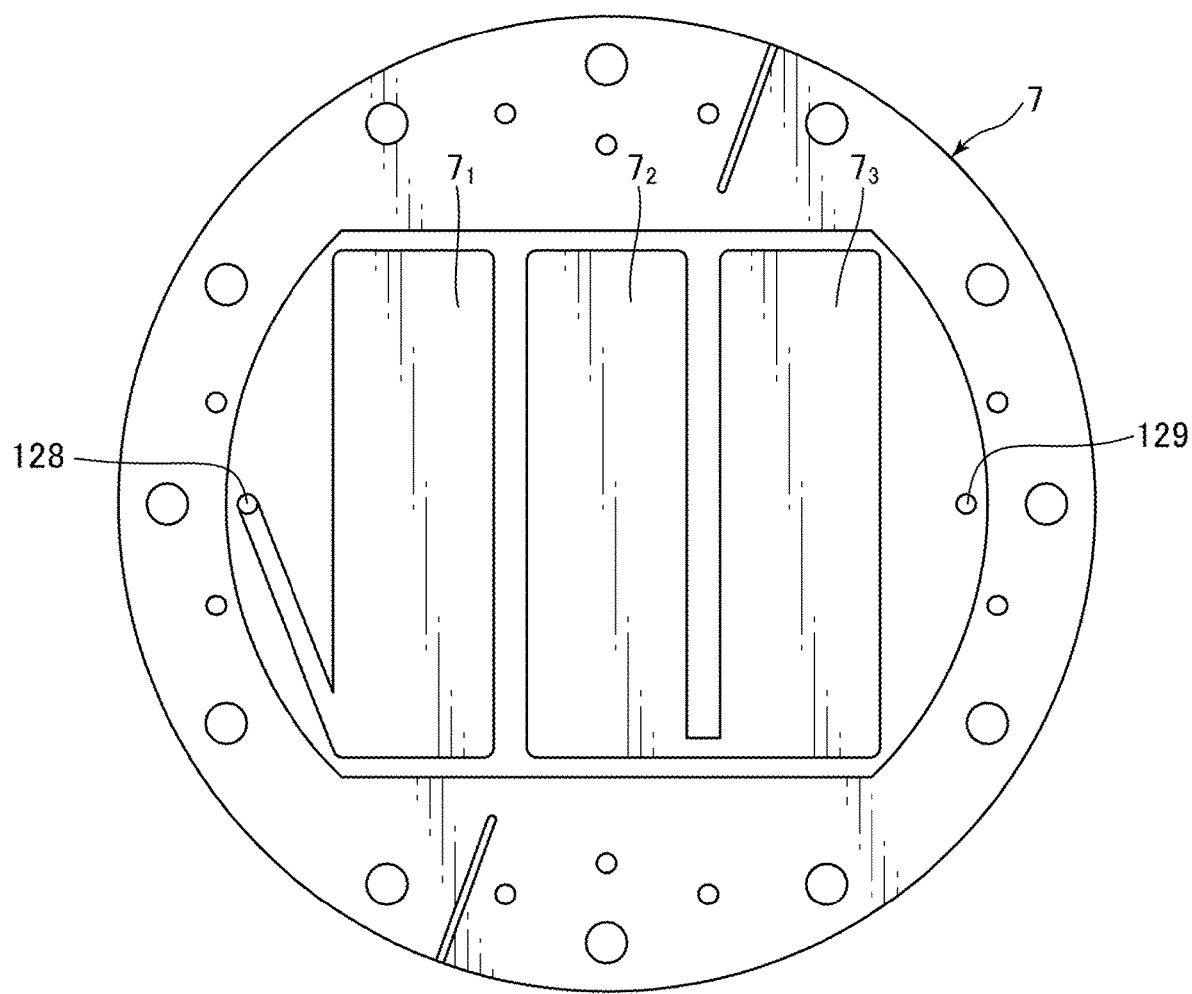
FIG. 14 is a front view of a Sabatier reaction plate.

A Sabatier reaction plate 7 is disposed adjacent to a gasket for Sabatier reaction 5 as shown in FIG. 13. FIG. 14 is a front view of the Sabatier reaction plate 7. As shown in FIG. 14, three rectangular concave parts $7_1$, $7_2$, $7_3$ are formed on the Sabatier reaction plate 7, and three Sabatier reaction catalysts 6 ($6_1$, $6_2$, $6_3$), which are depicted independently of the Sabatier reaction plate 7 in FIG. 13 and the like, are fitted into the concave parts $7_1$, $7_2$, $7_3$ of the Sabatier reaction plate 7 when the device is assembled. Then, the Sabatier reaction plate 7 and the gasket for Sabatier reaction 5 are brought into tightly contact with each other, and the Sabatier reaction catalysts 6 ($6_1$, $6_2$, $6_3$) are sandwiched therebetween and internally sealed thereby.

The Sabatier reaction catalysts 6 ($6_1$, $6_2$, $6_3$) include a Sabatier catalyst supported by a porous metal mesh. This is obtained by impregnating a porous metal mesh with a liquid catalyst followed by drying in one example.

The mixed gas containing hydrogen and carbon dioxide once discharged to the outside of the device from the gas outlet 125 is introduced inside the device again from a gas inlet 126 and sent to a small hole 127 provided at the gasket for Sabatier reaction 5 as shown in FIG. 13. The part denoted by sign 128 in FIG. 14 corresponds to the position of the small hole 127 of the gasket for Sabatier reaction 5, and the mixed gas containing hydrogen and carbon dioxide sent to the small hole 127 provided at the gasket for Sabatier reaction 5 is introduced into the Sabatier reaction plate 7 through this part.

Figure 15:
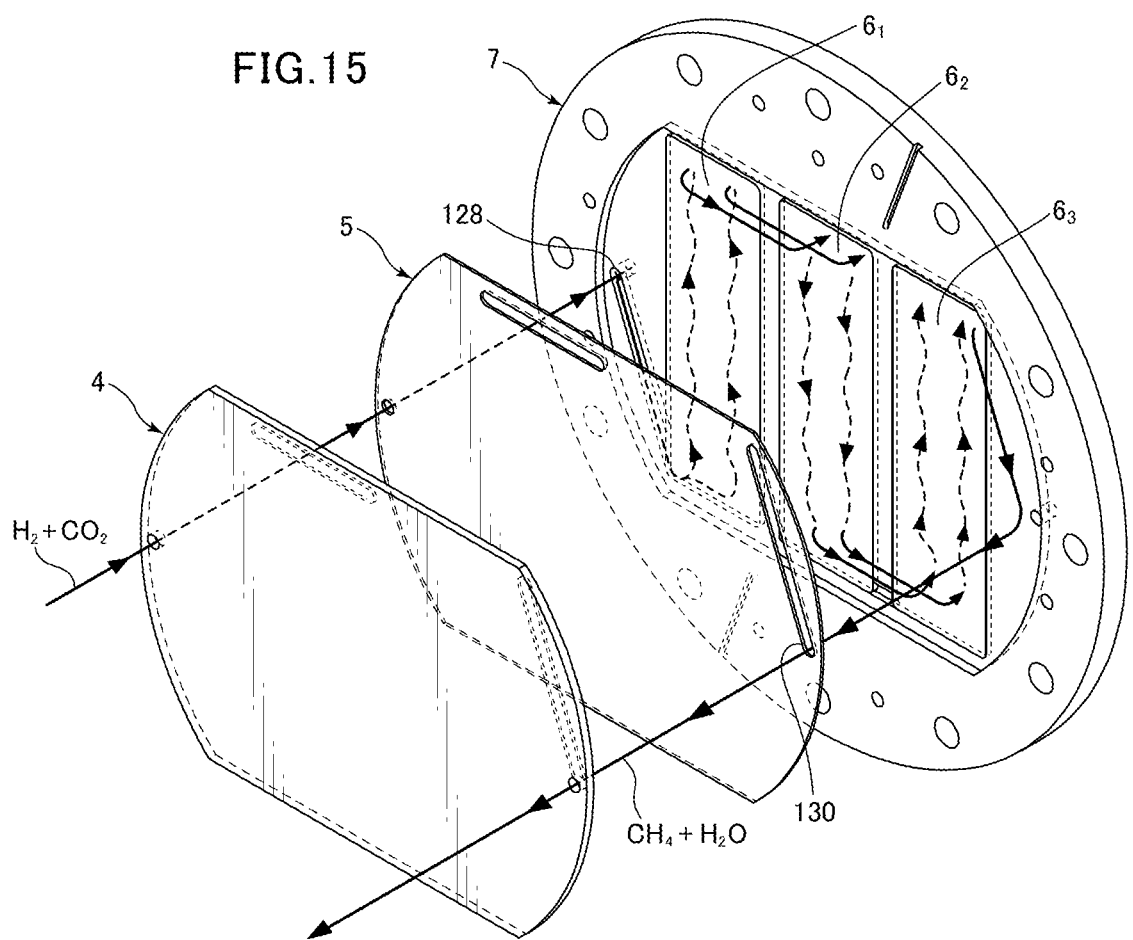
FIG. 15 explains how gas flows in the Sabatier reaction plate.

FIG. 15 explains how gas flows in the Sabatier reaction plate 7. The mixed gas containing hydrogen and carbon dioxide introduced into the Sabatier reaction plate 7 is firstly supplied to a lower part of the Sabatier reaction catalyst $6_1$ and flows upward inside the Sabatier reaction catalyst $6_1$ therefrom. The mixed gas having reached an upper part of the Sabatier reaction catalyst $6_1$ once exits from the Sabatier reaction catalyst $6_1$, flows toward the Sabatier reaction catalyst $6_2$ in a lateral direction through a manifold provided inside the cover plate 4 and the gasket 5, which are provided so as to tightly contact with each other, as shown in FIG. 15, and is supplied to the Sabatier reaction catalyst $6_2$ from an upper part of the Sabatier reaction catalyst $6_2$. The mixed gas having entered the Sabatier reaction catalyst $6_2$ flows downward inside the Sabatier reaction catalyst $6_2$. The mixed gas having reached a lower part of the Sabatier reaction catalyst $6_2$ once exits the Sabatier reaction catalyst $6_2$ and flows toward the Sabatier reaction catalyst $6_3$ in a lateral direction through a manifold inside the cover plate 4 and the gasket 5, is supplied to the Sabatier reaction catalyst $6_3$ from a lower part of the Sabatier reaction catalyst $6_3$, flows upward inside the Sabatier reaction catalyst $6_3$, and reaches an upper part of the Sabatier reaction catalyst $6_3$.

In this manner, the following Sabatier reaction $$4H_2 + CO_2 \rightarrow CH_4 + 2H_2O$$

occurs while the mixed gas containing hydrogen and carbon dioxide passes through the Sabatier reaction catalysts $6_1$, $6_2$, $6_3$, and methane gas and gas of water (water vapor) are generated. As described above, as gas flows across sufficiently long distance in the Sabatier reaction catalysts in the Sabatier reaction plate 7, introduced hydrogen and carbon dioxide are almost completely changed to methane gas and gas of water by Sabatier reaction.

Generated methane gas and gas of water are carried to a part denoted by sign 129 in FIG. 14 in the Sabatier reaction plate. This position corresponds to a small hole 130 provided at the gasket for Sabatier reaction 5, and methane gas and gas of water flow to a gas outlet 131 provided at the end plate 2 from the small hole 130 as shown in FIG. 13. In this manner, generated methane gas is finally obtained from the outlet 131. The obtained methane gas is made available for various applications such as being stored as an energy carrier.

In FIG. 3, FIG. 9, FIG. 10, FIG. 11, and FIG. 13, components exploded in the direction of the arrow 101 are shown in order to describe the configuration of the methane synthesis device 100 and the flow of the various kinds of fluid. However, a methane synthesis device 100 actually assembled is very thin and compact as shown in FIG. 1(b). Further, the water electrolysis unit and the Sabatier reaction unit are integrated. Since the methane synthesis device 100 is thin and compact as described above, the flowing pathways of various kinds of gas and liquid in the direction parallel to the arrow 101 inside the methane synthesis device 100 are understood to be very short. Therefore, hydrogen generated by the water decomposition unit is mixed with carbon dioxide in the gas mixing plate 9 shortly thereafter, immediately supplied to the Sabatier reaction catalysts $6_1$, $6_2$, $6_3$, and supplied for methane generation.

Incidentally, water electrolytic reaction is an endothermic reaction, and Sabatier reaction is an exothermic reaction. As in the present embodiment, by virtue of bringing the water electrolysis unit and the Sabatier reaction unit into tightly contact with each other, the latent heat of water used for water electrolysis is utilized, and heat generated by Sabatier reaction is effectively utilized. Consequently, enhancement of water electrolytic reaction efficiency and prevention of thermal runaway of the methane synthesis device as a whole are made possible. In this manner, by virtue of allowing water electrolytic reaction and Sabatier reaction to simultaneously proceed, methane may be synthesized with energy utilization efficiency higher than input electric energy without thermodynamic inconsistencies.

Embodiment 2

Figure 16:
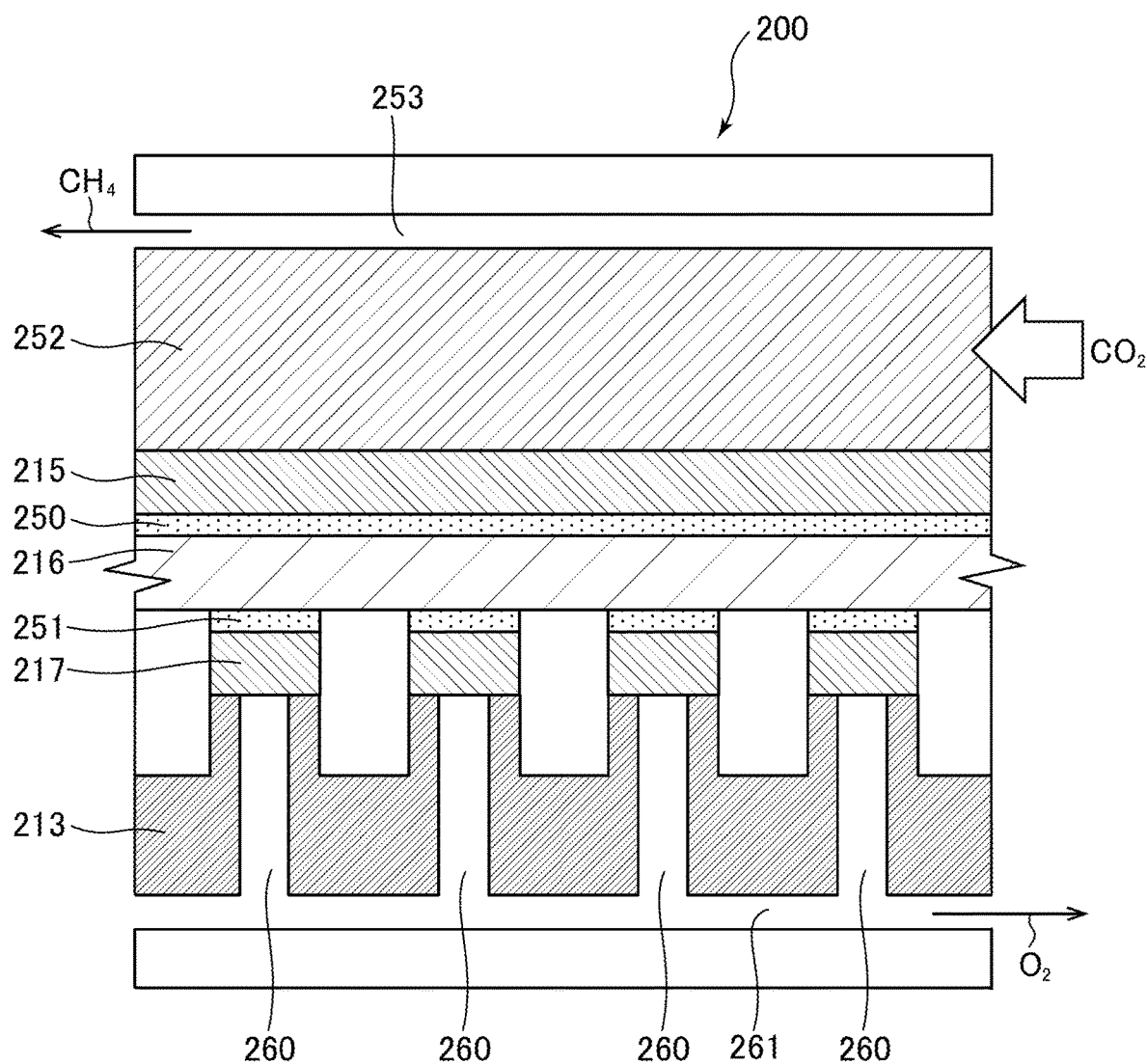
FIG. 16 is a schematic cross-sectional view showing a part of a methane generation device according to Embodiment 2 of the present invention.

FIG. 16 is a schematic cross-sectional view showing a part of a methane generation device 200 according to Embodiment 2 of the present invention, the figure corresponding to FIG. 8 in Embodiment 1. As with the case of FIG. 8, an electrolyte membrane 216 is also interposed between a hydrogen side above the electrolyte membrane 216 and an oxygen side below the electrolyte membrane 216 in FIG. 16. However, a gas separator 213 is provided in a lower side, that is, the oxygen side in the figure, and water is supplied from the oxygen side to the electrolyte membrane 216 in this embodiment. Therefore, an oxygen side electrode membrane 217 is provided with slits as shown in FIG. 7, and the slits are aligned with corresponding grooves provided at the gas separator 213 as with the case of FIG. 7. Then, as with the case of Embodiment 1, water is supplied to a surface of the electrolyte membrane 216 through a water flow passage and a number of grooves provided inside the gas separator 213. It is also similar to Embodiment 1 that catalyst layers 250, 251 having been subjected to water repellent treatment are respectively formed on surfaces of a hydrogen side electrode membrane 215 and the oxygen side electrode membrane 217, with each of the surfaces being on the side joining the electrolyte membrane 216.

A Sabatier reaction catalyst membrane 252 is disposed on the hydrogen side electrode membrane 215 so that the Sabatier reaction catalyst membrane 252 contacts with the hydrogen side electrode membrane 215. This Sabatier reaction catalyst membrane 252 is obtained by impregnating a porous metal mesh with a liquid catalyst followed by drying as with the case of the Sabatier reaction catalysts $6_1$, $6_2$, $6_3$ in Embodiment 1.

On water electrolysis, when negative voltage and positive voltage are applied to the hydrogen side electrode membrane 215 and the oxygen side electrode membrane 217, respectively, oxygen gas generated at the interface (catalyst layer) between the oxygen side electrode membrane 217 and the electrolyte membrane 216 permeates ladder-shaped members of the oxygen side electrode membrane 217, and is finally discharged to the outside through corresponding gas flow passages 260 and 261 provided at the gas separator 213. On the other hand, hydrogen gas generated at the interface (catalyst layer) between the hydrogen side electrode membrane 215 and the electrolyte membrane 216 permeates the planar hydrogen side electrode membrane 215 and passes through the Sabatier reaction catalyst membrane 252.

As shown in FIG. 16, carbon dioxide gas is supplied to the Sabatier reaction catalyst membrane 252 from the side in the figure. Sabatier reaction occurs between the carbon dioxide gas supplied from the outside and the hydrogen gas generated by water electrolysis inside the Sabatier reaction catalyst membrane 252 to generate methane gas. The generated methane gas is output to the outside through a gas flow passage 253 (methane gas flowing unit) provided in an upper part of the Sabatier reaction catalyst membrane 252, for example.

In this manner, when the Sabatier reaction catalyst membrane 252 is disposed so as to contact with the hydrogen side electrode membrane 215, enhancement of water electrolytic reaction efficiency and prevention of thermal runaway of the methane synthesis device as a whole are made possible by utilizing the latent heat of water used for water electrolysis and effectively utilizing heat generated by Sabatier reaction as described in relation to Embodiment 1. Furthermore, since the Sabatier reaction catalyst membrane 252 and the hydrogen side electrode membrane 215 are allowed to be disposed more closely, the effect is further enhanced.

Incidentally, while carbon dioxide gas is supplied from the right side on FIG. 16 in Embodiment 2, a configuration in which carbon dioxide is supplied from both sides is possible. In addition, a configuration in which carbon dioxide is supplied to the entire surface of the Sabatier reaction catalyst membrane 252 from an upper part on FIG. 16 is also possible.

Incidentally, while there is such a description that gas such as hydrogen is once discharged to the outside of the device in the embodiments, it does not mean that a gas outlet and a gas inlet are connected by piping or the like and gas is released to the outside of the device.

EXPLANATIONS OF LETTERS OR NUMERALS 4 cover plate
5 gasket for Sabatier reaction
6, $6_1$, $6_2$, $6_3$ Sabatier catalyst
7 Sabatier reaction plate
8 cover plate
9 gas mixing plate
13, 19, 213 gas separator
14, 18 gasket
15, 215 hydrogen side electrode membrane
16, 216 electrolyte membrane
17, 217 oxygen side electrode membrane
$35_1$, $36_1$ catalyst layer
$46_1$-$46_7$ ladder-shaped member
$60_1$-$60_6$ groove
$61_1$-$61_5$ plate-like part
$62_1$-$62_7$ gas flow passage
$63_1$, $63_2$ water flow passage
100, 200 methane synthesis device
110 water inlet
111 water outlet
112, 113, 114, 115, 125, 131 gas outlet
116, 117, 126 gas inlet
250, 251 catalyst layer
252 Sabatier reaction catalyst membrane
260, 261 gas flow passage

The invention claimed is:

1. A methane synthesis device comprising a water electrolysis unit including a hydrogen side electrode membrane, an electrolyte membrane, an oxygen side electrode membrane, and a water supplying section supplying liquid water from any of a side of the hydrogen side electrode membrane and a side of the oxygen side electrode membrane to a surface of the electrolyte membrane;
    a Sabatier reaction unit provided adjacent to the water electrolysis unit;
    a carbon dioxide supplying unit supplying carbon dioxide-containing gas to the Sabatier reaction unit; and a hydrogen gas supplying unit supplying hydrogen gas generated through electrolyzation of water in the water electrolysis unit to the Sabatier reaction unit, wherein the water electrolysis unit and the Sabatier reaction unit are stacked in a direction of thickness of the electrolyte membrane, and wherein methane gas is synthesized by a Sabatier reaction between the carbon dioxide-containing gas and the hydrogen gas supplied to the Sabatier reaction unit.

2. The methane synthesis device according to claim 1, wherein the water electrolysis unit, the Sabatier reaction unit, the carbon dioxide supplying unit, and the hydrogen gas supplying unit are integrally stacked.

3. The methane synthesis device according to claim 1, wherein heat of reaction generated in the Sabatier reaction unit is supplied to the water electrolysis unit.

* * * * *